United States Patent
McDaniel

(10) Patent No.: US 6,773,390 B2
(45) Date of Patent: Aug. 10, 2004

(54) RADIOACTIVE SOURCE RIBBON ASSEMBLY

(75) Inventor: Benjamin David McDaniel, Newport Beach, CA (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 10/102,085

(22) Filed: Mar. 20, 2002

(65) Prior Publication Data

US 2003/0181782 A1 Sep. 25, 2003

(51) Int. Cl.[7] .......................... A61N 5/00; A61M 36/00
(52) U.S. Cl. ................................. 600/3; 600/7
(58) Field of Search .................... 600/1–8; 252/478, 252/644, 645; 800/431, 433, 435, 436, 585; 228/138; 206/438, 524.1; 250/506.1, 507.1, 496.1; 424/1.11; 604/187; 976/DIG. 351; 378/20; 588/11; 29/460

(56) References Cited

U.S. PATENT DOCUMENTS

| | | | | |
|---|---|---|---|---|
| 3,351,049 A | * | 11/1967 | Lawrence | 600/8 |
| 4,208,588 A | * | 6/1980 | Rudin | 250/496.1 |
| 4,819,618 A | * | 4/1989 | Liprie | 600/7 |
| 4,861,520 A | * | 8/1989 | van't Hooft et al. | 252/644 |
| 4,891,165 A | * | 1/1990 | Suthanthiran | 600/8 |
| 5,503,614 A | * | 4/1996 | Liprie | 600/7 |
| 5,807,231 A | * | 9/1998 | Liprie | 600/3 |
| 5,833,593 A | * | 11/1998 | Liprie | 600/3 |
| 5,857,956 A | * | 1/1999 | Liprie | 600/7 |
| 6,019,718 A | * | 2/2000 | Hektner | 600/3 |
| 6,254,552 B1 | * | 7/2001 | Lewis et al. | 600/3 |
| 6,319,188 B1 | * | 11/2001 | Lovoi | 600/3 |
| 6,458,069 B1 | * | 10/2002 | Tam et al. | 600/3 |
| 6,482,143 B1 | * | 11/2002 | Slater et al. | 600/8 |
| 6,485,405 B1 | * | 11/2002 | Liprie | 600/3 |
| 6,485,406 B1 | * | 11/2002 | Ziegler et al. | 600/8 |
| 6,497,646 B1 | * | 12/2002 | Candelaria et al. | 600/7 |
| 6,497,647 B1 | * | 12/2002 | Tucker | 600/8 |
| 6,505,392 B1 | * | 1/2003 | Liprie | 29/460 |

* cited by examiner

Primary Examiner—Eric F. Winakur
Assistant Examiner—Nikita R Veniaminov
(74) Attorney, Agent, or Firm—Carl J. Evans

(57) ABSTRACT

A radioactive source ribbon assembly may be reusably utilized in conjunction with a delivery sheath or catheter for delivering therapeutic dosages of ionizing radiation to various anatomical regions. The radioactive source ribbon assembly comprises an outer jacket formed from or coated with a lubricious coating for insertion into the delivery sheath or catheter. The assembly also comprises a radiation resistant sleeve formed from a braided structure which encapsulates a radioactive source and core. The braided structure is the primary axial load bearing member of the assembly and functions as such without sacrificing assembly flexibility.

22 Claims, 3 Drawing Sheets

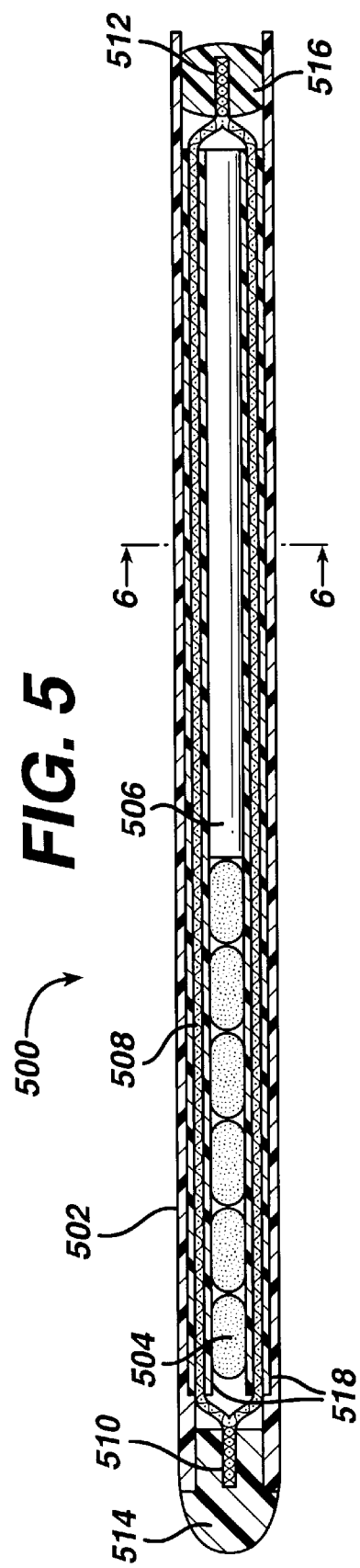
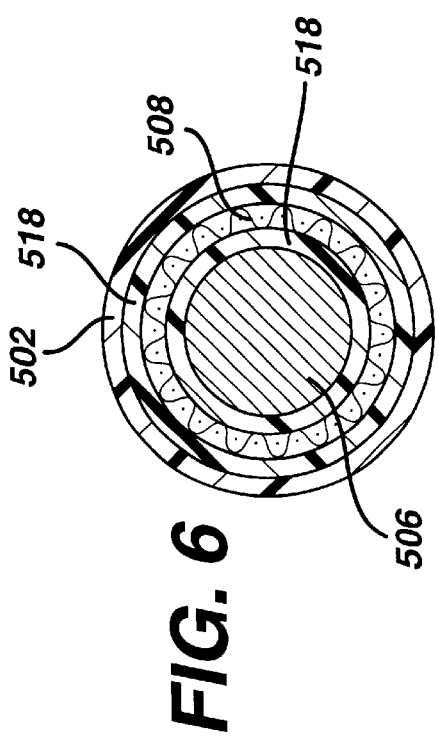
FIG. 5
FIG. 6

RADIOACTIVE SOURCE RIBBON ASSEMBLY

BACKGROUND OF THE INVENTION

1. Field of the Invention

The present invention relates to brachytherapy devices, and more particularly to an increased strength, flexible, radioactive source ribbon assembly having an additional containment layer.

2. Discussion of the Related Art

Percutaneous transluminal coronary angioplasty (PTCA) is a therapeutic medical procedure used to increase blood flow through an artery and is the predominant treatment for coronary vessel stenosis. The increasing popularity of the PTCA procedure is attributable to its relatively high success rate and its minimal invasiveness compared with coronary by-pass surgery. Patients treated utilizing PTCA; however, may suffer from restenosis. Restenosis refers to the re-narrowing of an artery after a successful angioplasty procedure. Restenosis usually occurs within the initial six months after an angioplasty. Early attempts to alleviate the effect of restenosis included repeat PTCA procedures or by-pass surgery, with attendant high cost and added patient risk.

Restenosis is now believed to occur at least in part as a result of injury to the arterial wall during the lumen opening angioplasty procedure. In some patients, the injury initiates a repair response that is characterized by hyperplastic growth of the vascular smooth muscle cells in the region traumatized by the angioplasty. Intimal hyperplasia or smooth muscle cell proliferation narrows the lumen that was opened by the angioplasty, regardless of the presence of a stent, thereby necessitating a repeat PTCA or use of other procedures to alleviate the restenosis.

Recent studies indicate that intravascular radiotherapy (IRT) has promise in the prevention or long-term control of restenosis following angioplasty. Intravascular radiotherapy may also be used to prevent or delay stenosis following cardiovascular graft procedures or other trauma to the vessel wall. Proper control of the radiation dosage; however, appears to be important to inhibit or substantially arrest hyperplasia without causing excessive damage to healthy tissue. Underdosing will result in inadequate inhibition of smooth muscle cell hyperplasia, or possibly even exacerbation of hyperplasia and resulting restenosis.

Radiation therapy may also be utilized in the treatment of other diseases such as cancerous and non-cancerous tumors or other proliferative normal tissue disorders. In this type of therapy, the ultimate aim is to destroy the malignant tissue without causing excessive radiation damage to nearby healthy and possibly vital tissue. This is difficult to accomplish because of the proximity of malignant tissue to healthy tissue.

Brachytherapy is a form of radiation treatment in which an ionizing radiation source, for example, an intravascular radiotherapy source ribbon, is placed into or adjacent to a tumor or stenotic lesion. Although any number of radioactive substances and/or radioactive sources may be utilized in brachytherapy, Iodine-125 is currently a good candidate isotope for vascular brachytherapy. Iodine-125 has been used as a liquid or immobilized onto a variety of surfaces for diagnostic and therapeutic purposes. It has already been fashioned into a variety of shapes and used clinically for cancer treatment as briefly described above.

SUMMARY OF THE INVENTION

The radioactive source ribbon assembly of the present invention provides a means for overcoming the difficulties associated with the devices currently in use as briefly described above.

In accordance with one aspect, the present invention is directed to a radioactive source ribbon assembly. The radioactive source ribbon assembly comprises an outer jacket adapted for use with a delivery catheter, a radiation resistant load bearing sleeve mounted within the outer jacket, and a radioactive source positioned within the radiation resistant load bearing sleeve.

In accordance with another aspect, the present invention is directed to a radioactive source ribbon assembly. The radioactive source ribbon assembly comprises a substantially tubular outer jacket having a proximal end and a distal end, the substantially tubular outer jacket being adapted for use with a delivery catheter, a substantially tubular radiation resistant axial load bearing sleeve mounted with the outer jacket, a radioactive source positioned in a distal portion of the radiation resistant axial load bearing sleeve, a core positioned in a proximal portion of the radiation resistant axial load bearing sleeve adjacent to the radioactive source and proximal and distal seals mounted to the proximal and distal ends of the substantially tubular jacket for sealing the jacket.

In accordance with another aspect, the present invention is directed to a radioactive source ribbon assembly. The radioactive source ribbon assembly comprises a substantially tubular outer jacket having a proximal end and a distal end, the substantially tubular outer jacket being adapted for use with a delivery catheter, a substantially tubular radiation resistant axial load bearing sleeve mounted within the outer jacket, a substantially tubular inner jacket mounted within the substantially tubular radiation resistant axial load bearing sleeve, a radioactive source positioned in a distal portion of the substantially tubular inner jacket, a core positioned in a proximal portion of the substantially tubular inner jacket, and proximal and distal seals mounted to the proximal and distal ends of the substantially tubular outer jacket for sealing the outer jacket.

In accordance with another aspect, the present invention is directed to a radioactive source ribbon assembly. The radioactive source ribbon assembly comprises a substantially tubular outer jacket having a proximal end and a distal end, the substantially tubular outer jacket being adapted for use with a delivery catheter, a substantially tubular radiation resistant axial load bearing member encapsulated in an inner jacket and mounted within the outer jacket, a radioactive source positioned in a distal portion of the encapsulated substantially tubular radiation resistant axial load bearing member, a core positioned in a proximal portion of the encapsulated substantially tubular radiation resistant axial load bearing member, and proximal and distal seals mounted to the proximal and distal ends of the substantially tubular outer jacket for sealing the outer jacket.

The radioactive source ribbon assembly of the present invention is utilized to deliver therapeutic doses of radiation to various regions of the human anatomy. The radioactive source ribbon assembly comprises an inner assembly and an outer jacket. The inner assembly includes a radioactive source, a core and a radiation resistant sleeve. The radioactive source and the core are encased in the radiation resistant sleeve to provide increased axial strength for the source ribbon assembly. The outer jacket comprises a lubricious material, for example, a polymeric material which encases the inner assembly. The radioactive source ribbon assembly is delivered to the appropriate region of the human anatomy via a sheath or catheter. Accordingly, the lubricious material forming the outer jacket provides a reduced friction interface for ease of insertion and removal of the assembly from the sheath or catheter.

The radiation resistant sleeve may be formed from any number of radiation resistant materials such as stainless steel. The radiation resistant sleeve comprises a braided tubular structure which encapsulates the radioactive source and the core. The braided tubular structure provides the assembly with increased tensile strength without sacrificing flexibility. In addition, the braided structure allows for an expanded number of materials to be used for the outer jacket by serving as the primary axial load member of the assembly and reducing concerns related to the strength degradation of the outer jacket. The radiation resistant sleeve also provides a secondary containment layer in the unlikely event of an outer jacket breach.

The radioactive source ribbon assembly of the present invention may be utilized any number of times over a given predetermined period of time. Once the predetermined period of time is achieved, the entire assembly is disposed of according to well-known radioactive disposal practices.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 5 is a longitudinal cross-sectional view of another alternate exemplary embodiment of a radioactive source ribbon assembly in accordance with the present invention.

FIG. 6 is a transverse cross-sectional view of the radioactive source ribbon assembly of FIG. 5 taken along section line 6—6.

DETAILED DESCRIPTION OF THE PREFERRED EMBODIMENTS

The radioactive source ribbon assembly of the present invention may be utilized to deliver therapeutic doses of ionizing radiation for the acute and long term treatment of restenosis and related vascular disease, as well as other diseases such as cancerous and non-cancerous or other proliferative normal tissue disorders. The radioactive source ribbon assembly may be delivered to a treatment site via a delivery sheath or catheter.

Figure 1:
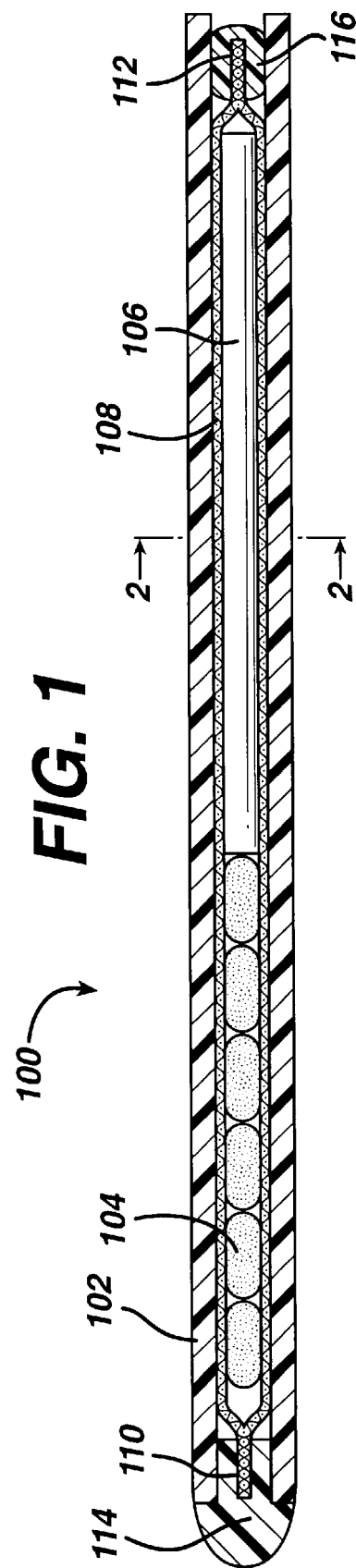
FIG. 1 is a longitudinal cross-sectional view of an exemplary embodiment of a radioactive source ribbon assembly in accordance with the present invention.

In one exemplary embodiment, illustrated in FIG. 1, the radioactive source ribbon assembly 100 comprises an inner assembly and an outer jacket 102. The inner assembly includes a radioactive source 104, a core 106, a radiation resistant sleeve 108 which encases the radioactive source 104 and the core 106, and first and second ends 110, 112 for securing the radioactive source 104 and the core 106 within the radiation resistant sleeve 108. The radioactive source ribbon assembly 100 also comprises distal and proximal seals 114, 116 for sealing the inner assembly within the outer jacket 102.

The outer jacket 102 comprises a substantially tubular container which is sealed at both its proximal and distal ends to isolate the radioactive source 104. The substantially tubular container may be formed from any suitable biocompatible and radioactive emission transparent material which is both flexible enough and stiff enough to navigate through narrow and/or tortuous pathways. In addition, the substantially tubular container is preferably formed from a material that has sufficient lubricity to allow the radioactive source ribbon assembly 100 to be easily guided through the delivery sheath or catheter. Delivery sheaths and/or catheters are well known in the relevant art. Alternately, the substantially tubular container and/or the delivery sheath or catheter may be coated with a lubricious material to facilitate relative movement therebetween. In one exemplary embodiment, the substantially tubular container comprises a polymeric material, for example, Nylon®.

Figure 2:
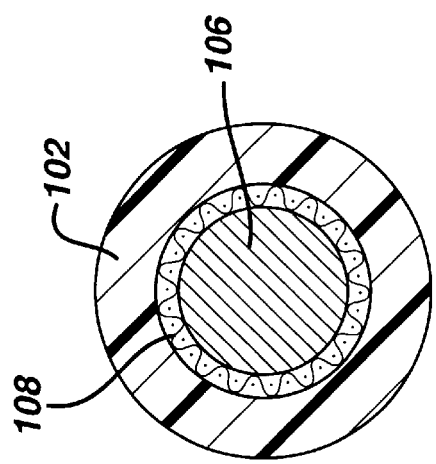
FIG. 2 is a transverse cross-sectional view of the radioactive source ribbon assembly of FIG. 1 taken along section lines 2—2.

In the exemplary embodiment, the outer jacket 102 comprises a substantially tubular container having a substantially circular cross-section as illustrated in FIG. 2. Alternate designs may include non-circular cross-sections. In addition, the outer jacket 102 may be formed from other materials, including tubing, heat shrink material, spray or dip coatings, binary adhesives, or any material that forms a lubricious outer covering and a primary containment layer. In yet another alternate embodiment, the outer jacket 102 may be formed from one material and then coated with a lubricious second material. The lubricious coating may comprise any suitable biocompatible material. One such lubricious coating may be silicone. Other materials which may be utilized include water soluble powders such as vitamin C, an antioxidant, or an anti-coagulant such as aspirin or heparin.

The radioactive source 104 may include any therapeutic amount of radioactive material appropriately distributed on a carrier body or core. The carrier body or core may be formed from any suitable material which is detectable by x-rays for proper positioning in the body, and to which the requisite therapeutic amount of radioactive material may be affixed. In one exemplary embodiment, the carrier body or core comprises at least one section or length of solid silver wire, or silver plated wire, and the radioactive material comprises radioisotopes such as Iodine-125 and Iodine-171. It is important to note that other radioactive substances may be utilized.

Silver is the material of choice for a carrier body or core because it provides good x-ray visualization, which is important for proper positioning of the seed during therapy and because radioactive materials such as radioactive iodine may be easily affixed to the surface thereof by chemical or electroplating processes. It is obvious that other x-ray opaque materials such as gold, copper, and iron may be plated with silver to form a carrier body equivalent to a solid silver rod for purposes of the present invention. Similarly, silver may be deposited, chemically or by using sputtering and ion plating techniques, onto a substrate other than metal, for example, polymers such as polypropylene filament, provided that the thickness of the silver coating on the substrate exceeds about 0.050 mm to ensure adequate x-ray visualization.

Radioactive iodine may be attached to a silver substrate by a variety of suitable means, such as by first chloriding or bromiding the silver to form a layer of insoluble silver chloride or silver bromide, and then replacing the chloride or bromide ions with radioactive iodine ions by simple ion exchange. This process as well as other processes are well known in the relevant art.

The radioactive source 104 may comprise a number of sections of radioactive material covered wires. These individual sections are typically referred to as seeds. The seeds may be adjacent one another in the radioactive source ribbon assembly 100 or they may be spaced apart by any suitable means. Spacers serve two main functions. The first function is to space the seeds a sufficient distance to control the dose rate profile and lower the total radioactivity of the source. The second function is to increase the flexibility of the source ribbon assembly.

In an alternate exemplary embodiment, iridium seeds may be utilized as the radioactive source. The size and number of seeds is selected to provide a therapeutic dosage of radiation to a particular region of the anatomy as described above.

The radioactive source 104 may comprise any suitable profile. For example, the carrier body or core may utilize modified cross-section wires to increase the surface area upon which the radioactive substance may be deposited without increasing the overall size of the source. In addition, the modified cross-section wires may be designed in such a manner as to reduce the distance a photon directed inwardly rather than outwardly would have to travel through the wire, thereby reducing attenuation.

The core 106 of the radioactive source ribbon assembly 100 enhances the pushability of the assembly 100, as well as providing a level of stiffness/kink resistance. Essentially, the core 106 provides sufficient pushability to allow the radioactive source ribbon assembly 100 to be delivered to the distal end of the delivery sheath or catheter at the treatment site, and a sufficient level of stiffness/kink resistance to facilitate rapid insertion of the assembly 100 via manual or automated delivery.

The core 106 preferably comprises the same cross-sectional shape as the radioactive source 104 and the other components comprising the radioactive source ribbon assembly 100, and may be formed from a wide variety of materials. The core 106 may be formed from metallic materials, including ferrous and non-ferrous metals, such as stainless steel, nickel titanium, titanium alloy, steel alloy, as long as the stiffness and kink resistance required for its intended use are maintained. The core 106 may comprise a solid element, one or more solid elements twisted, twined or braided together, or a hollow core element.

The distal end of the core 106 is adjacent to the proximal end of the radioactive source 104. In one exemplary embodiment, the distal end of the core 106 directly contacts the proximal end of the radioactive source 104. In another alternate exemplary embodiment, a buffer formed from any suitable material may be utilized at the junction between the core 106 and the radioactive source 104. If a buffer material is utilized, the material should preferably be radioactive resistant and radiopaque. In yet another alternate exemplary embodiment, zone heat treating may be embodied in the core 106 material to optimize the transition between the proximal end of the radioactive source 104 and the distal end of the core 106. If heat treating is utilized, the core 106 would have increased flexibility towards the radioactive source 104. A hybrid core comprising multiple materials, construction elements and heat treated conditions may also be utilized.

In yet another alternate exemplary embodiment, the radioactive source 104 and the core 106 may comprise a unitary or one piece structure. For example, the core 106 may comprise a main, non-radioactive section and a radioactive distal section, for example, formed from silver and radioactive iodine as described above.

The radiation resistant sleeve 108 encapsulates both the radioactive source 104 and the core 106. As briefly described above, the radiation resistant sleeve 108 serves as the primary axial load bearing member in the radioactive source ribbon assembly 100. In addition, the radiation resistant sleeve 108 acts as a secondary containment layer for the radioactive source 104. In the unlikely event of a breach of the outer jacket 102, the radiation resistant sleeve 108 prevents the radioactive source 104 from separating from the assembly 100.

The radiation resistant sleeve 108 may comprise a substantially tubular configuration having an inside diameter equal to or slightly less than the outside diameter of the core 106 and the radioactive source 104, and an outside diameter equal to or slightly less than the inside diameter of the outer jacket 102. In one exemplary embodiment, the radiation resistant sleeve 108 comprises a braided structure which surrounds both the radioactive source 104 and the core 106. A braided structure is utilized to increase the axial and tensile strength of the radioactive source ribbon assembly 100 without decreasing the flexibility of the assembly. In addition, the braided structure allows for the choice of an expanded selection of polymers which may be utilized for the outer jacket 102 by serving as the primary axial load bearing member for the radioactive source ribbon assembly 100. Also, as the primary axial load bearing member for the assembly 100, there is less of a concern for the strength degradation of the outer jacket material.

The braided structure may be constructed from any number of radiation resistant materials, including ferrous and non-ferrous metallic materials such as stainless steel, nickel titanium alloy, titanium alloy, and steel alloys. In addition to metallic materials, the braided structure may be constructed from fibers such as fibers sold under the tradename Kevlar®, carbon fiber or other radiation resistant fibers having strength properties sufficient to act as the primary axial load bearing member during the intended usage life of the assembly 100. The particular type of braid structure may vary depending on a number of factors, including the type of material utilized in constructing the braid structure. For example, the number and size of the individual fibers or threads comprising the braid structure may effect the braid pattern. As with the other components of the radioactive source ribbon assembly 100, the cross-sectional shape of the braided structure may be varied.

Another important consideration in determining the material from which the radiation resistant sleeve 108 is fabricated is the type of radioactive source 104. For example, if an isotope of iodine is utilized as the radioactive source 104, a stainless steel radiation resistant sleeve 108 may result in a too high attenuation factor; accordingly, a less dense material may be required. If; however, a higher energy emission source such as iridium is utilized, stainless steel would be suitable for sleeve construction.

Once the radioactive source 104 and the core 106 are positioned within the radiation resistant sleeve 108, the ends 110, 112 of the braided structure forming the radiation resistant sleeve 108 are closed to completely encase the radioactive source 104 and the core 106. The ends 110, 112 of the braided structure may be closed in any number of ways. In one exemplary embodiment, the ends 110, 112 of the braided structure may simply be twisted together. The twisting of the ends 110, 112 not only functions to completely encase the radioactive source 104 and the core 106, but also to ensure that the braided structure is the primary axial load bearing member. The twisting of the ends 110, 112 may resemble the twisting on the ends of common candy wrappers. The ends 110, 112 of the braided structure may also be sealed in a variety of other ways. For example, the braided structure may be sewn together at its ends 110, 112 utilizing another component such as a metallic wire or polymeric filament which is radiation resistant. Other means include welding the ends 110, 112 of the braided structure closed, welding a sealing component or plug in position, swaging, crimping or bending a sealing ring or clamp to the ends 110, 112, lashing, wrapping, or knotting the ends 110, 112, and using an adhesive to fasten the ends 110, 112 in a restrictive position.

The completed inner assembly is positioned within the outer jacket 102 and sealed therein. As mentioned above, the radiation resistant sleeve 108 is a secondary containment means; accordingly, the outer jacket 102 is the primary containment means. It is important that the radioactive material be contained within the radioactive source ribbon assembly to prevent potential contamination. The inner assembly may be sealed within the outer jacket 102 by any suitable means. In one exemplary embodiment, the proximal and distal seals 116, 114 may be separate structures. In other words, the proximal and distal seals 116, 114 may comprise the same or different material than that of the outer jacket 102, and which may be attached to the outer jacket 102 by any number of suitable methods. Regardless of the material utilized, the proximal and distal seals 116, 114 may be attached to the outer jacket 102 utilizing various means, including adhesives, ultra sonic welding, melting, compression welding, threads or any other suitable means. Alternately, the ends of the outer jacket 102 may simply be melted to form sealed ends.

The proximal and distal seals 116, 114 may take any suitable form, but preferably conform to the cross-sectional shape of the outer jacket 102. The distal seal 114 is preferably shaped to facilitate easy access to the lumen of the delivery sheath or catheter. In the illustrated exemplary embodiment, the distal seal 114 has a rounded nose; however, as stated above, the distal seal 114 or plug may be spherical, elliptical, tapered, chamfered, or blunt with or without a broken outer edge. The proximal plug 116 may be of similar design or any other suitable design. In an alternate design, a proximal seal may not be necessary.

It is important that the transition or seams between the proximal and distal seals 116, 114 and the outer jacket 102 be as smooth as possible so as to minimize the risk of kinking within the delivery sheath or catheter.

Figure 3:
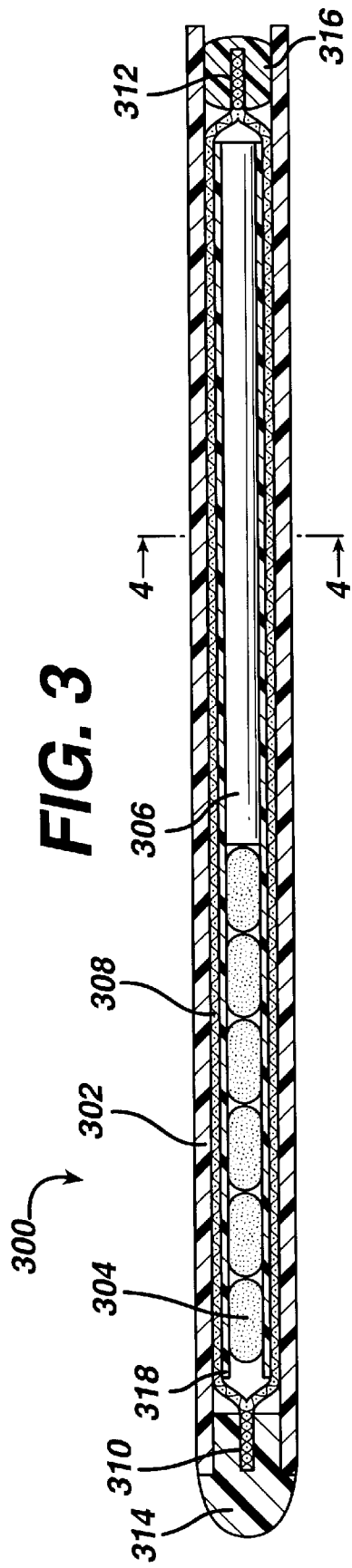
FIG. 3 is a longitudinal cross-sectional view of an alternate exemplary embodiment of a radioactive source ribbon assembly in accordance with the present invention.
Figure 4:
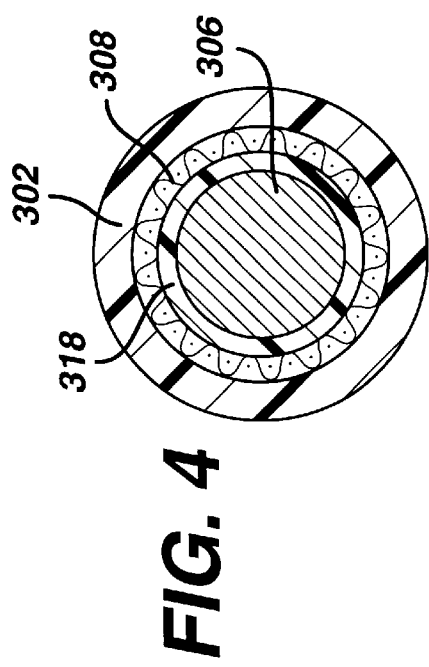
FIG. 4 is a transverse cross-sectional view of the radioactive source ribbon assembly of FIG. 3 taken along section line 4—4.

In an alternate exemplary embodiment, illustrated in FIG. 3, the radioactive source ribbon assembly 300 may comprise an inner jacket 318 in addition to an outer jacket 302, a radioactive source 304, a core 306, a radiation resistant sleeve 308, first and second ends 310, 312 and distal and proximal seals 314, 316. In this exemplary embodiment, the radiation resistant sleeve 308 may be sandwiched between the outer jacket 302 and the inner jacket 318. The inner jacket 318 may be formed from the same material as the outer jacket 302 or a different biocompatible, radiation emission opaque material. FIG. 4 provides a clear illustration of the radiation resistant sleeve 308 sandwiched between the outer jacket 302 and the inner jacket 318.

In yet another alternate exemplary embodiment, illustrated in FIG. 5, the radiation resistant sleeve 508 may be embedded in an inner jacket 518. The outer jacket 502, the radioactive source 504, the core 506, the first and second ends 510, 512 and the distal and proximal seals 514, 516 are the same as described with respect to the exemplary embodiments described above. FIG. 6 clearly illustrates the radiation resistant sleeve 508 embedded in the inner jacket 518.

In yet another alternate exemplary embodiment, the radioactive source ribbon assembly may be terminated at the end of the radioactive source section. In this embodiment, a separate core section may be attached to the proximal end of the radioactive source section by any suitable means to provide sufficient axial strength for the assembly.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A radioactive source ribbon assembly comprising:
   an outer jacket adapted for use with a delivery catheter;
   a radiation resistant load bearing sleeve mounted within the outer jacket, the radiation resistant load bearing sleeve comprises a braided structure, the braided structure being the primary axial load bearing member of the assembly; and
   a radioactive source positioned within the radiation resistant load bearing sleeve.

2. The radioactive source ribbon assembly according to claim 1, wherein the outer jacket comprises a biocompatible and radioactive emission transparent material.

3. The radioactive source ribbon assembly according to claim 2, wherein the outer jacket comprises a polymeric material.

4. The radioactive source ribbon assembly according to claim 1, wherein the braided structure is sealed at its ends.

5. The radioactive source ribbon assembly according to claim 4, wherein the braided structure comprises stainless steel.

6. The radioactive source ribbon assembly according to claim 5, wherein the radioactive source is encased in a distal portion of the braided structure.

7. The radioactive source ribbon assembly according to claim 6, wherein the radioactive source comprises one or more radioactive elements.

8. A radioactive source ribbon assembly comprising:
   a substantially tubular outer jacket having a proximal and a distal end, the substantially tubular outer jacket being adapted for use with a delivery catheter;
   a substantially tubular radiation resistant axial load bearing sleeve mounted within the outer jacket, the radiation resistant load bearing sleeve comprises a braided structure, the braided structure being the primary axial load bearing member of the assembly;
   a radioactive source positioned in a distal portion of the radiation resistant axial load bearing sleeve;
   a core positioned in a proximal portion of the radiation resistant axial load bearing sleeve adjacent to the radioactive source; and
   proximal and distal seals mounted to the proximal and distal ends of the substantially tubular jacket for sealing the jacket.

9. The radioactive source ribbon assembly according to claim 8, wherein the substantially tubular outer jacket comprises a biocompatible, radioactive emission transparent material.

10. The radioactive source ribbon assembly according to claim 9, wherein the substantially tubular outer jacket comprises a lubricious material.

11. The radioactive source ribbon assembly according to claim 9, wherein the substantially tubular outer jacket comprises a lubricious coating.

12. The radioactive source ribbon assembly according to claim 8, wherein the ends of the braided structure are sealed to ensure that the braided structure is the primary axial load bearing member of the assembly.

13. The radioactive source ribbon assembly according to claim 12, wherein the ends of the braided structure are sealed by twisting the ends of the braided structure.

14. The radioactive source ribbon assembly according to claim 13, wherein the radioactive source is encased in a distal portion of the braided structure.

15. The radioactive source ribbon assembly according to claim 14, wherein the radioactive source comprises one or more radioactive elements.

16. The radioactive source ribbon assembly according to claim 15, wherein the core comprises a radiation resistant material for increasing the pushability of the assembly.

17. The radioactive source ribbon assembly according to claim 16, wherein the proximal and distal seals comprise separate structures affixed to the proximal and distal ends of the outer jacket.

18. The radioactive source ribbon assembly according to claim 17, wherein the distal seal is configured for insertion into the delivery catheter.

19. The radioactive source ribbon assembly according to claim 16, wherein the proximal and distal seals and the outer jacket comprise a unitary structure.

20. The radioactive source ribbon assembly according to claim 8, wherein the core and the radioactive source comprise a unitary structure.

21. A radioactive source ribbon assembly comprising:

a substantially tubular outer jacket having a proximal end and a distal end, the substantially tubular outer jacket being adapted for use with a delivery catheter;

a substantially tubular radiation resistant axial load bearing sleeve mounted within the outer jacket;

a substantially tubular inner jacket mounted within the substantially tubular radiation resistant axial load bearing sleeve;

a radioactive source positioned in a distal portion of the substantially tubular inner jacket;

a core positioned in a proximal portion of the substantially tubular inner jacket; and proximal and distal seals mounted to the proximal and distal ends of the substantially tubular outer jacket for sealing the outer jacket.

22. A radioactive source ribbon assembly comprising:

a substantially tubular outer jacket having a proximal end and a distal end, the substantially tubular outer jacket being adapted for use with a delivery catheter;

a substantially tubular radiation resistant axial load bearing member encapsulated in an inner jacket and mounted within the outer jacket;

a radioactive source positioned in a distal portion of the encapsulated substantially tubular radiation resistant axial load bearing member;

a core positioned in a proximal portion of the encapsulated substantially tubular radiation resistant axial load bearing member; and proximal and distal seals mounted to the proximal and distal ends of the substantially tubular outer jacket for sealing the outer jacket.

* * * * *